United States Patent [19]
De Kler et al.

[11] Patent Number: 5,538,507
[45] Date of Patent: Jul. 23, 1996

[54] HYPODERMIC SYRINGE

[76] Inventors: Dirk De Kler, Meidoornlaan 37, NL-1231 CA Loosdrecht; Hendrik Diepbrink, Amstelveenseweg 159, NL-1075 XA Amsterdam, both of Netherlands

[21] Appl. No.: 982,635

[22] Filed: Nov. 27, 1992

[51] Int. Cl.$^6$ .................................................. A61M 5/32
[52] U.S. Cl. .................... 604/192; 604/195; 604/110; 604/272
[58] Field of Search .................... 604/192, 110, 604/195, 198, 263, 187, 207, 220, 246, 166, 208–211, 224, 228, 240, 241, 242, 272; 128/919

[56] References Cited

U.S. PATENT DOCUMENTS

| | | | |
|---|---|---|---|
| 4,790,822 | 12/1988 | Haining | 604/110 |
| 4,808,169 | 2/1989 | Haber et al. | 604/195 |
| 4,832,696 | 5/1989 | Luther et al. | 604/164 |
| 4,834,718 | 5/1989 | McDonald | 604/195 |
| 4,883,471 | 11/1989 | Braginetz et al. | 604/195 |
| 4,950,241 | 8/1990 | Ranford | 604/110 |
| 4,955,869 | 9/1990 | Bin | 604/195 |
| 5,085,638 | 2/1992 | Farbstein et al. | 604/110 |
| 5,290,233 | 3/1994 | Campbell | 604/110 |

*Primary Examiner*—C. Fred Rosenbaum
*Assistant Examiner*—V. Alexander
*Attorney, Agent, or Firm*—Antonio R. Durando; Harry M. Weiss

[57] ABSTRACT

A hypodermic needle system that comprises a hub engaging close-fittingly over the end portion of the cylinder of a syringe and coupling means that consists of flexible legs capable of gripping the proximal end of the needle. In another embodiment, the apparatus also comprises a connecting element that is fixedly attached to the needle and is releasably mounted inside the hub, and the coupling means consists of flexible legs capable of gripping the connecting element. As a result of these configurations, the number of components in the hypodermic syringes constructed according to this invention is limited and the products are relatively inexpensive to manufacture.

10 Claims, 6 Drawing Sheets

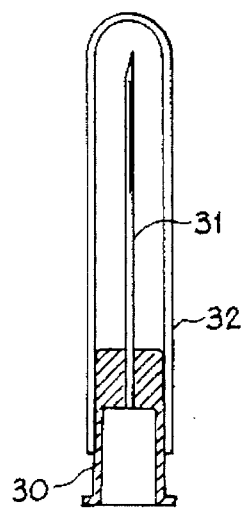
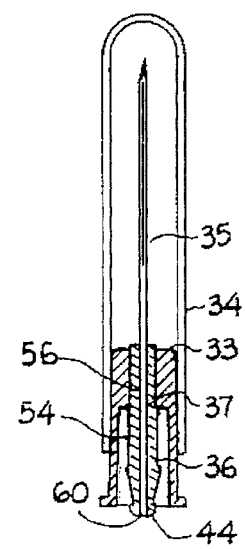
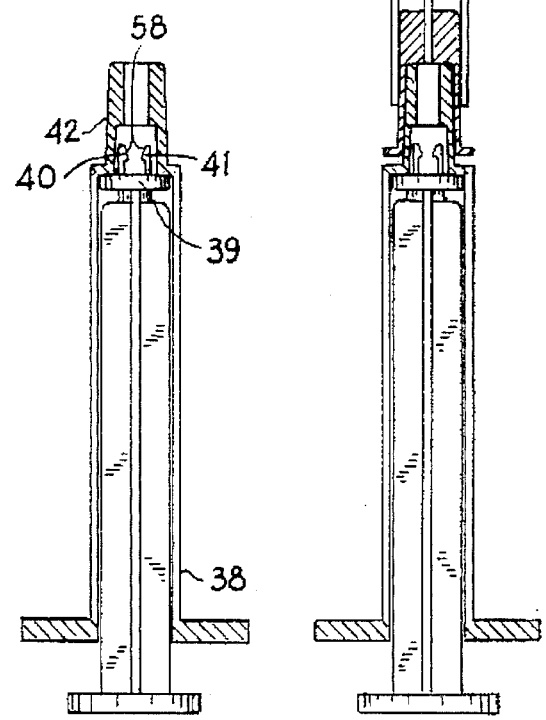
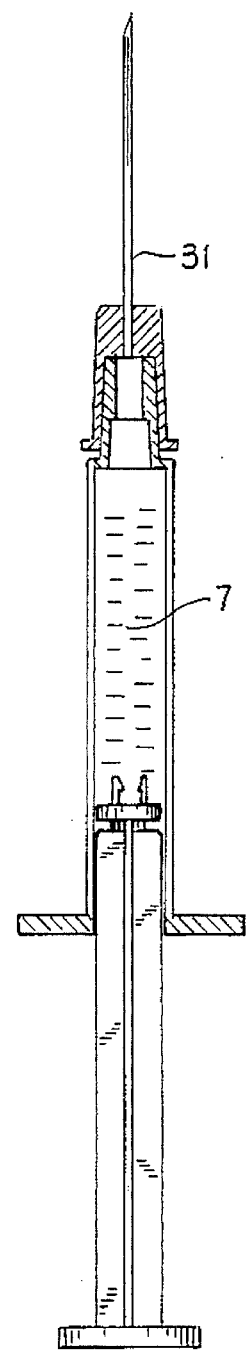
FIG.10  FIG.11  FIG.9  FIG.12  FIG.13

HYPODERMIC SYRINGE

BACKGROUND OF THE INVENTION

1. Field of the Invention

This invention is related in general to the field of medical devices for drug infusion and, in particular, to hypodermic syringes.

2. Description of the Related Art

In the process of using hypodermic needles it has become increasingly important to avoid accidental pricking of care providers which might result in the transmission of serious diseases. Thus, devices have been developed to protect a user by retracting the needle into the syringe after a hypodermic injection is performed.

The prior art describes hypodermic syringes comprising a cylinder with an end portion over which a hypodermic needle is releasably arranged, a piston slidably displaceable in the cylinder, and coupling means connected to the piston and co-acting with the hypodermic needle for connecting the piston and the hypodermic needle. Such a hypodermic syringe is described in U.S. Pat. No. 4,950,241.

In a known hypodermic syringe, a connecting piece is placed in the hypodermic syringe for coupling the piston with the hypodermic needle. During use, a needle with a hub is pushed onto the syringe in the usual manner, whereby the hub and the channel of the needle connect therein with the connecting piece. After injecting, the piston is coupled to the connecting piece by means of a coupling member and when the piston is retracted the connecting piece and the needle and hub placed thereon are pulled inside.

BRIEF SUMMARY OF THE INVENTION

It is an object of this invention to provide a hypodermic syringe consisting of a limited number of components that can be assembled simply and inexpensively to form the end product.

It is a further object of the invention that the components used be suitable for manufacture by an injection molding production process.

A final objective of this invention is the realization of the above mentioned goals in an economical and commercially viable manner.

These goals are achieved according to this invention by providing a hypodermic needle system that has a hub engaging close-fittingly over the end portion of the cylinder of a syringe and coupling means that consists of flexible legs capable of gripping the proximal end of the needle. In another embodiment, the apparatus also comprises a connecting element that is fixedly attached to the needle and is releasably mounted inside the hub, and the coupling means consists of flexible legs capable of gripping the connecting element. As a result of these configurations, the number of components in the hypodermic syringes constructed according to this invention is limited and the products are relatively inexpensive to manufacture.

In the process of injection, a mechanical coupling is effected between the piston and the needle, or the piston and the connecting element, by means of flexible legs that engage a notch in the shaft of the needle (or a retaining ridge in the connecting element). During coupling care must be taken to avoid an outward-directed movement of the needle, which might result in the needle penetrating further than desired into the patient. This is achieved by having the hub of the needle engage the cylinder close-fittingly, so that the clamping force of the hub over the cylinder is greater than the force exerted by the piston on the needle or the connecting element during coupling. Displacement of the hub and needle is thereby avoided.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose only some of the various ways in which the invention may be practiced.

BRIEF DESCRIPTION OF THE DRAWINGS

FIGS. 9–16 show a second embodiment of the invention.

DETAILED DESCRIPTION OF THE PREFERRED EMBODIMENTS

Figure 1:
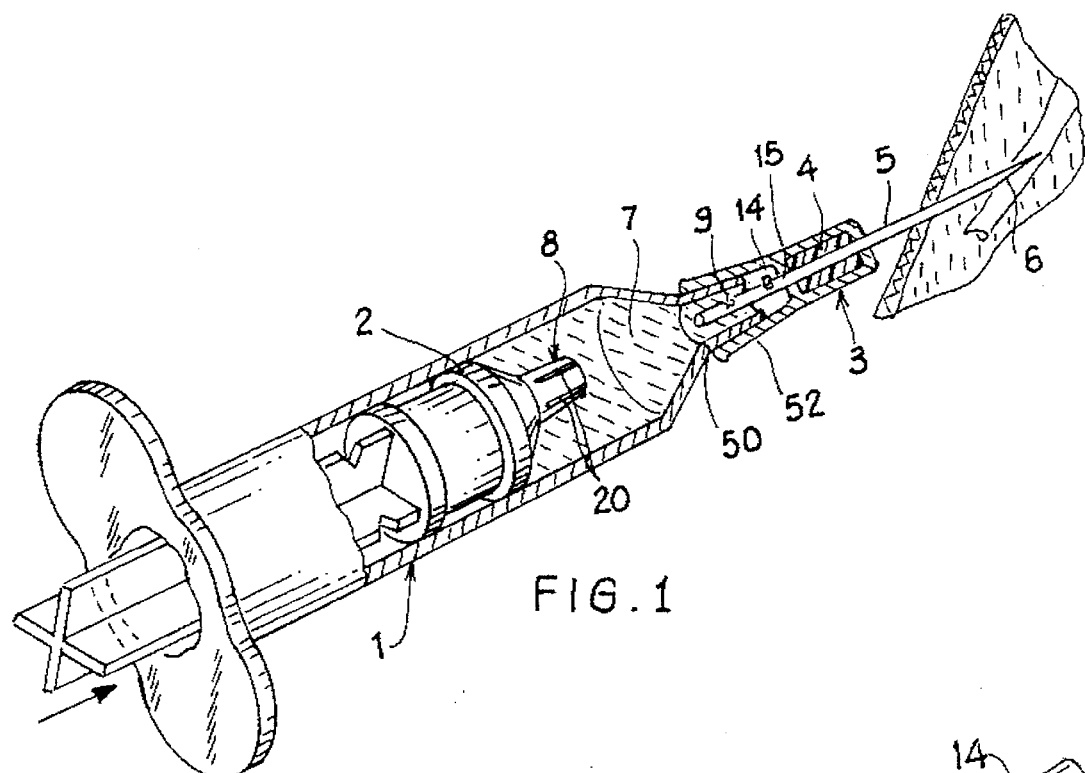
FIG. 1 shows a perspective view of a hypodermic syringe according to the invention.
Figure 3:
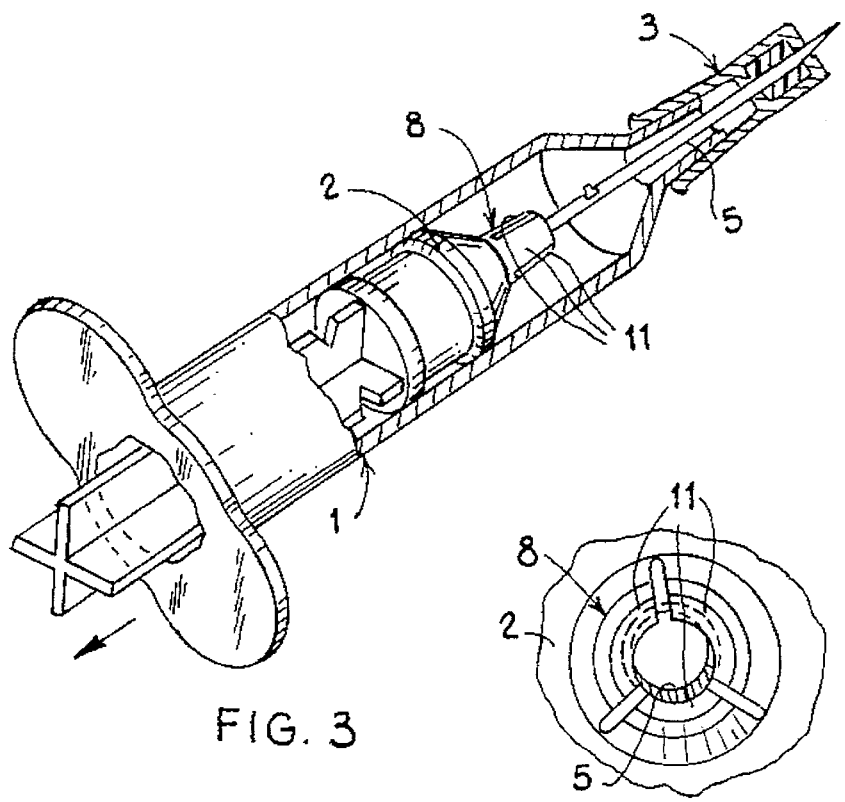
FIG. 3 is a view similar to FIG. 1, illustrating a different position of the hypodermic needle.

Referring to the drawings, wherein like parts are designated throughout with like numerals and symbols, FIG. 1 illustrates in perspective view the preferred embodiment of the hypodermic syringe of this invention. The syringe comprises a cylinder casing 1, wherein a piston 2 is ·slidably arranged. Firmly placed on the conical distal end 50 of the casing 1, as in the case of conventional syringes, is a fitting piece 3 having a conforming hub 52 that can be pressed against the end 50 for frictional connection therewith. The fitting piece 3 contains a needle 5 mounted coaxially with the fitting piece through a transverse wall 15 and slidably affixed to the fitting piece by means of a dense filler material 4. In typical manner, the needle is provided on its distal extremity with a sharpened penetrating end 6 in order to be able to insert the needle in the human body. A liquid 7 for injection is disposed in the cylinder space between the piston and the distal end 50 of the cylinder casing, which is plugged by the fitting piece 3 mounted thereon. When the piston is retracted proximally in the direction of the arrow in FIG. 3 after the liquid 7 has been injected, the needle is carried along inside the cylinder space as a result of the coupling between the end portion 8 of the piston and the needle 5, so that accidental pricking does not occur.

Figure 2:
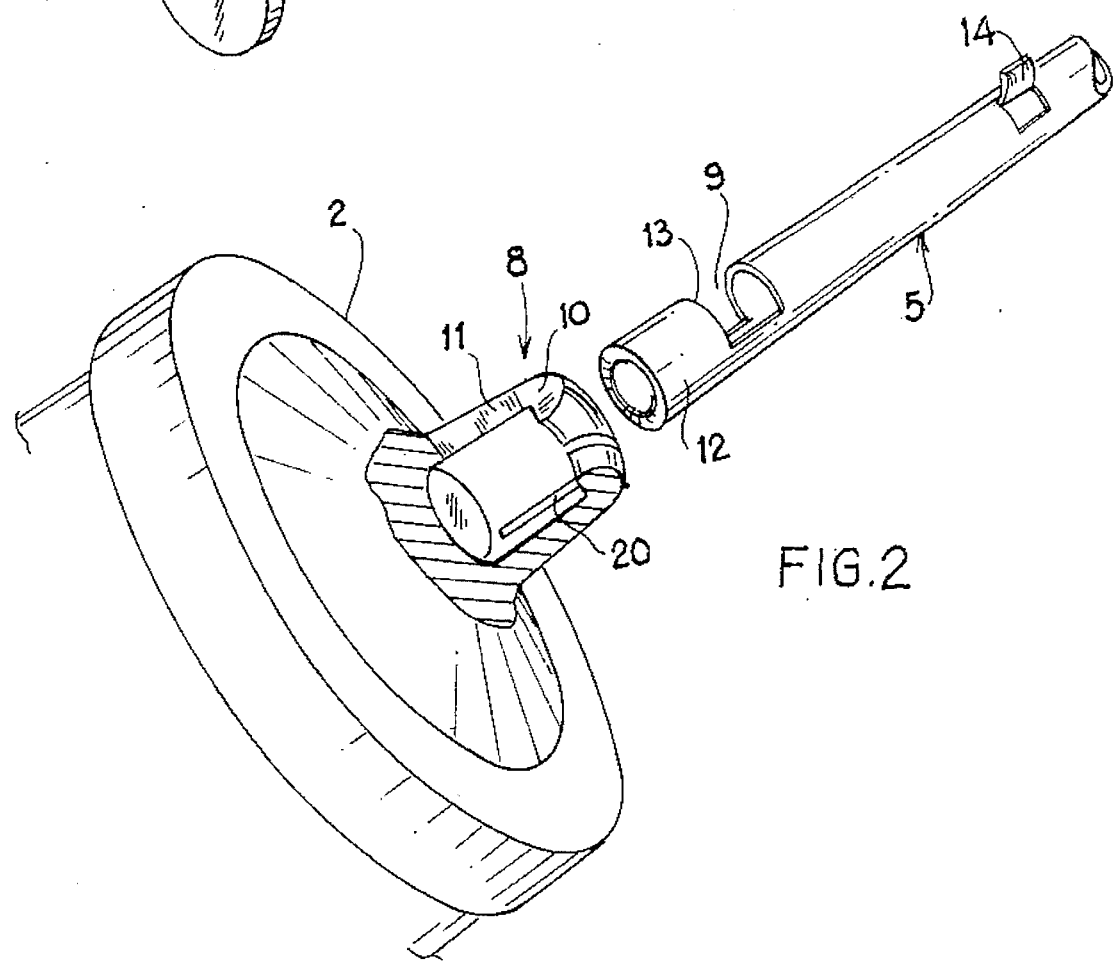
FIG. 2 is a perspective view of a detail of the coupling mechanism of the invention.
Figure 5:
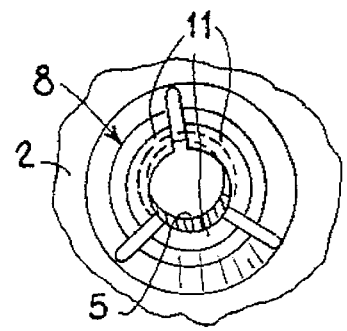
FIG. 5 is a cross-sectional view taken along line V—V in FIG. 4.
Figure 4:
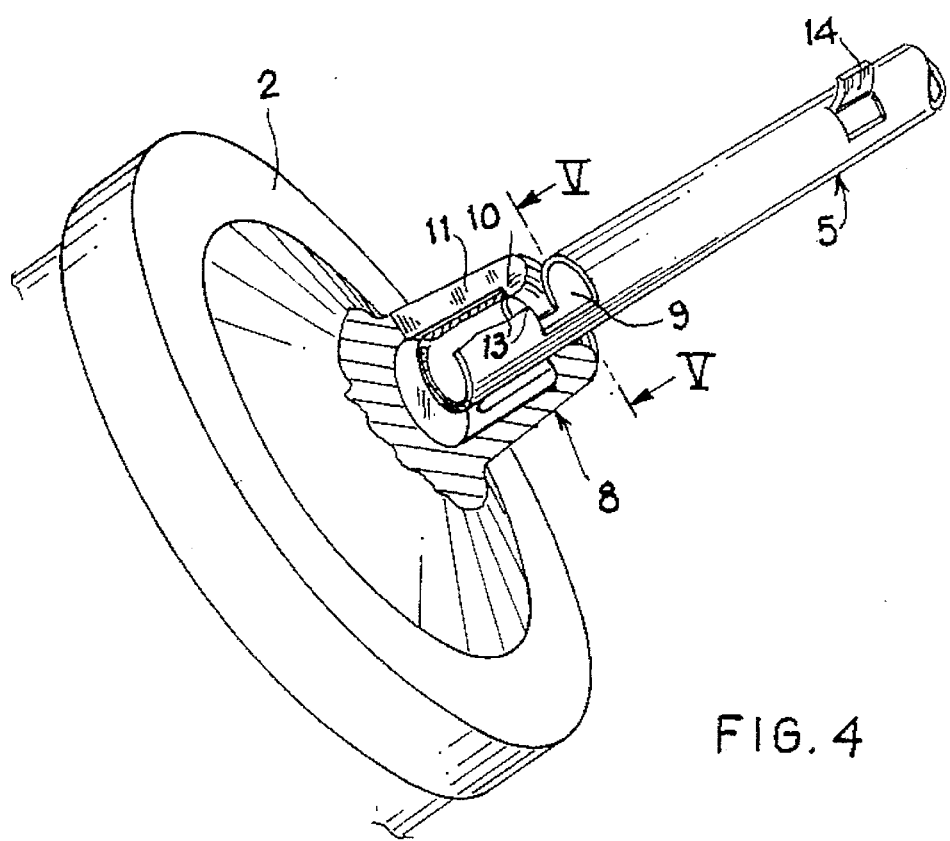
FIG. 4 is a view similar to FIG. 2, illustrating a different position of the needle.
Figure 7:
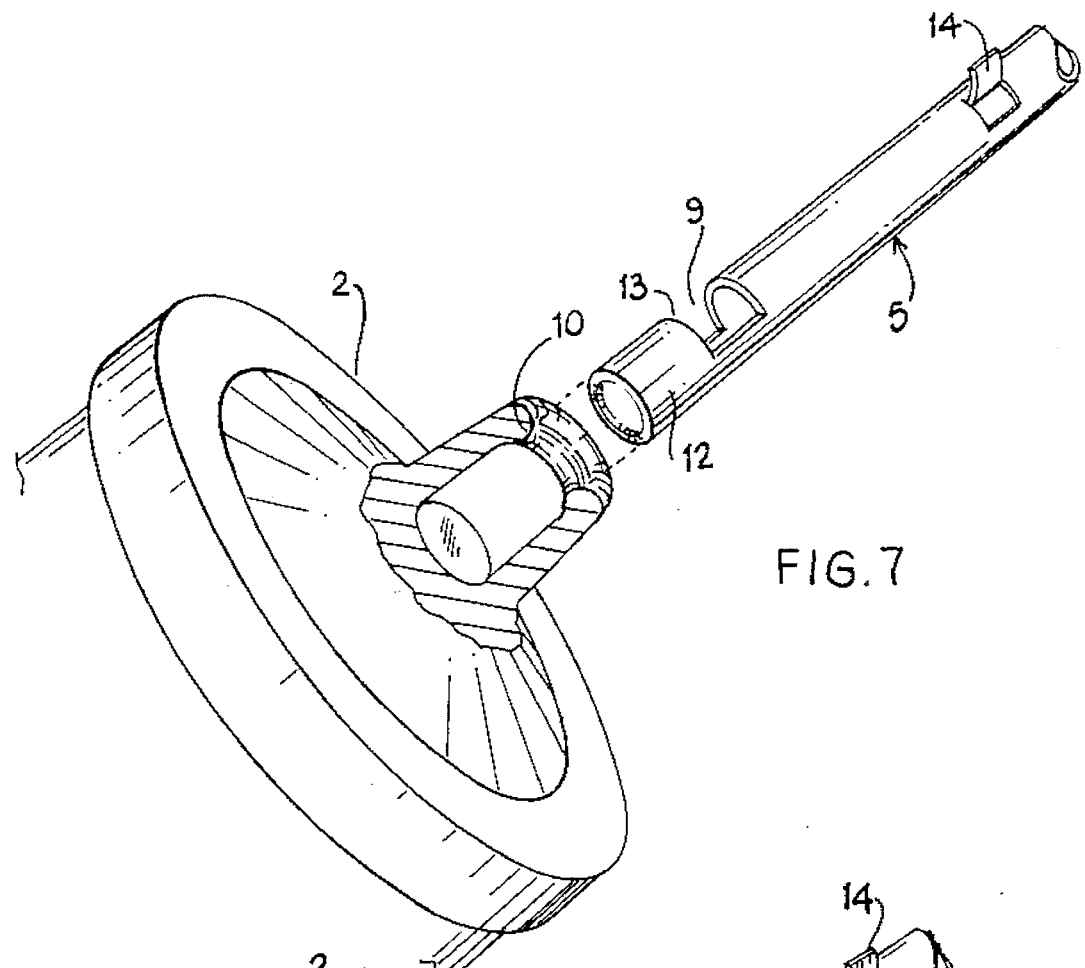
FIG. 7 shows an embodiment wherein the legs form part of a conical wall.
Figure 8:
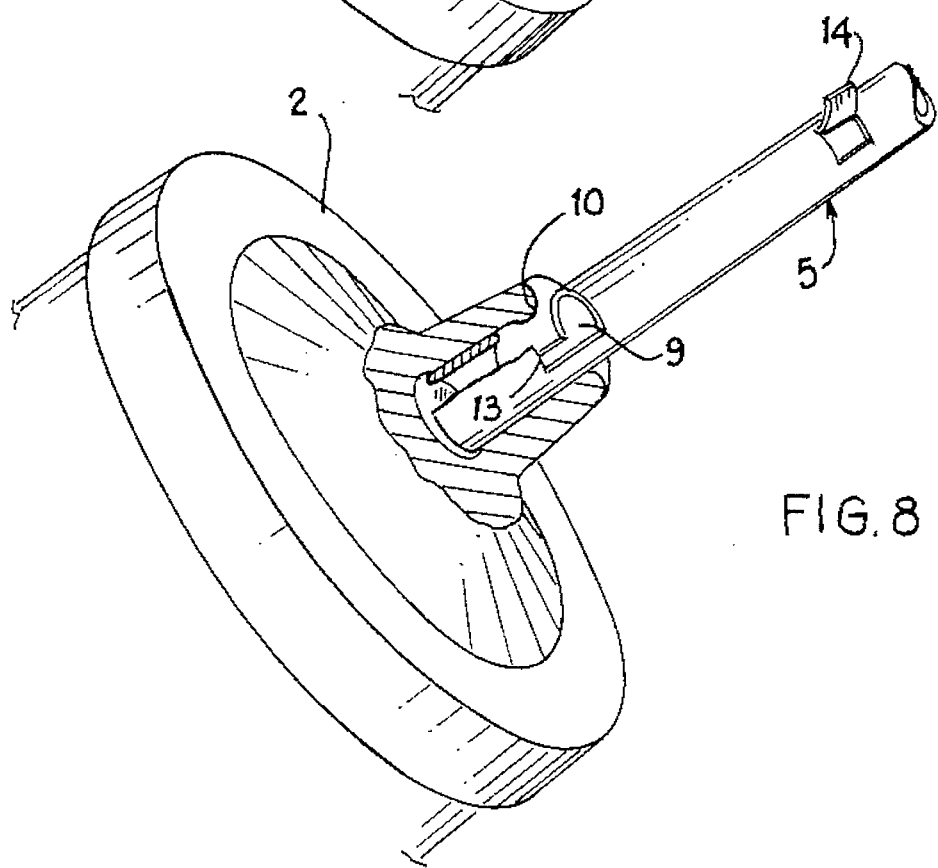
FIG. 8 is a view similar to FIG. 7, illustrating a different position of the needle.

The coupling mechanism according to the invention for effecting the connection between the needle 5 and the end portion 8 of the piston consists of a notch 9 in the shaft of the needle and of flexible legs 11 with inward ridges 10 in the end portion 8 of the piston 2. The member herein referred to as legs 11 may consist of the flexible wall of a cone-shaped member open at the top with an inward ridge 10, as seen in FIGS. 7 and 8; or it can consist of separate legs 11 with ridges 10 projecting inward and separated by longitudinal slits 20, such as in the embodiment shown in FIGS. 1 and 2. In the latter configuration, a number of such legs 11, each having a ridge 10, is arranged in a circle to form the substantially conical end portion 8 of the piston (FIG. 5). When the legs reach the proximal end 12 of the needle 5, they bend radially outward because of their flexible-material construction and, when they reach the notch 9, they snap inward behind the edge 13, thus effecting an operationally reliable coupling between the piston 2 and the needle 5.

The needle 5 is in addition provided with an outward curving lip 14 that is engaged by the transverse wall 15 of the fitting piece 3 in order to prevent the needle 5 from being carried too far into the body during the coupling of the needle and piston.

Figure 6:
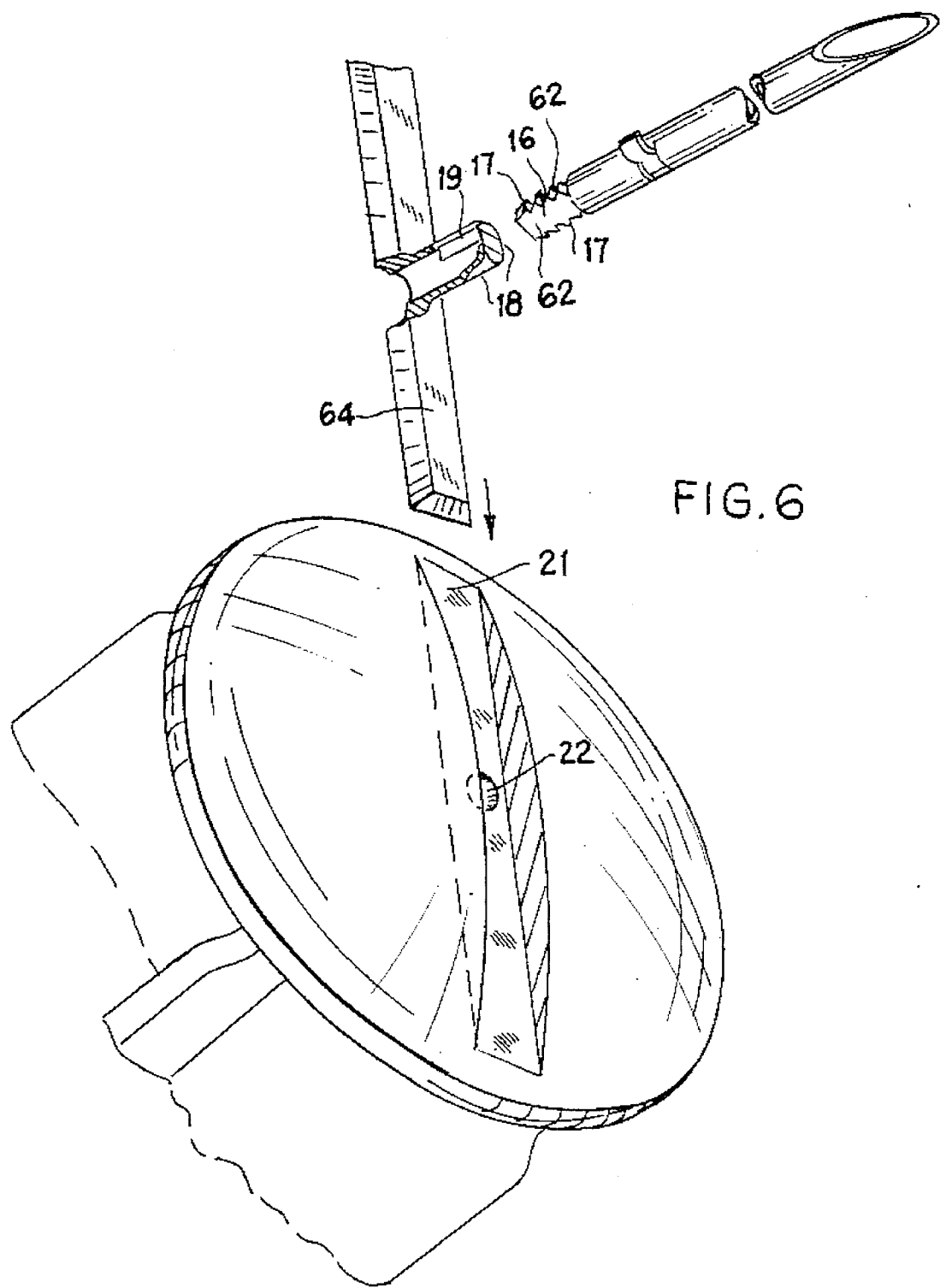
FIG. 6 shows an alternative embodiment of the needle and of the manner of affixing the flexible legs to the piston.

In the embodiment shown in FIG. 6, the proximal end 16 of the needle is flattened to form two opposite flat sides 62 (obviously, though, leaving sufficient room for the liquid 7 to be injected therethrough) and it is provided with cut-out notches 17 running transversely to the flat sides. Correspondingly, flexible legs 18 and 19 in the end portion 8 of the piston are disposed so as to allow free passage of the flattened proximal end 16 and lock behind the notches 17. The legs 18 and 19 are integral with a base member 64 that is oriented radially with respect to the piston. As illustrated in the figure, the base member 64 can be constructed so that it is removably attached to the piston in form-fitting manner within a groove 21 arranged in the distal end of the piston and conforming to the shape of the base member 64, so that it can be locked to the piston by means of a ball catch connection 22 (FIG. 6). This construction also enables the use of the hypodermic syringe without the described coupling means, so that universal use becomes possible.

In the embodiment illustrated in FIGS. 9–16, the apparatus also includes a suction needle and uses a separate connecting element between the needle and the flexible legs in the end portion of the piston. A suction needle 31 is affixed to a hub 30, as shown in FIG. 10, and a protective cap 32 is placed in the usual manner onto the hub 30. A hypodermic needle 35, shown in FIG. 11, likewise has a hub 33 equivalent in function to the hub 30 and a protective cap 34 pressure-fitted over the hub 33 in the same way as cap 32. The hypodermic needle 35 is threaded through a longitudinal bore 60 in a plastic connecting element 36 and is attached thereto by means of adhesive material. The bore in the connecting element 36 may have a diameter sufficiently large to permit needles with different diameters to be placed therein, thus requiring the bridging of any clearance between the bore and the needle by using a greater quantity of adhesive. The proximal end of the connecting element 36 contains a peripheral ridge 44 forming a lip functionally equivalent to the notches 17 of the needle shown in FIG. 6. The hub 33 contains a longitudinal distal bore 56 that makes it possible to close-fittingly mount it around the distal portion 37 of the connecting element 36.

Figure 14:
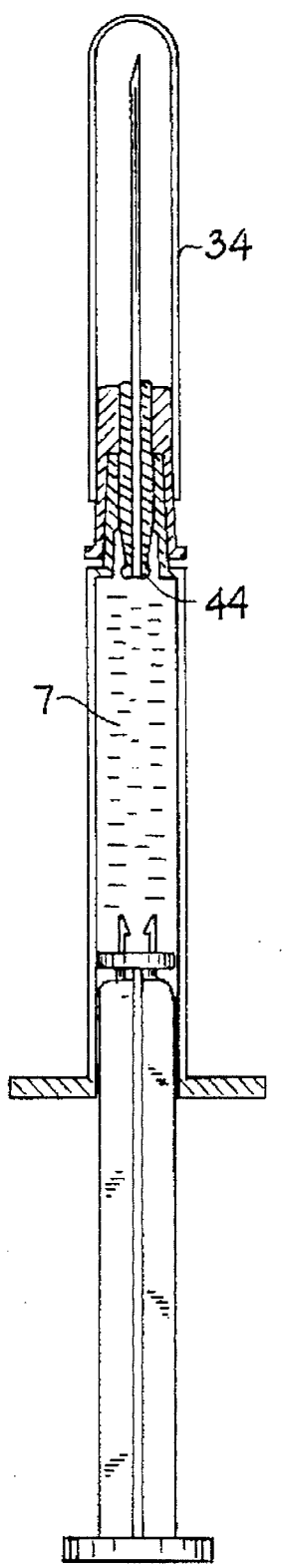
Figure 15:
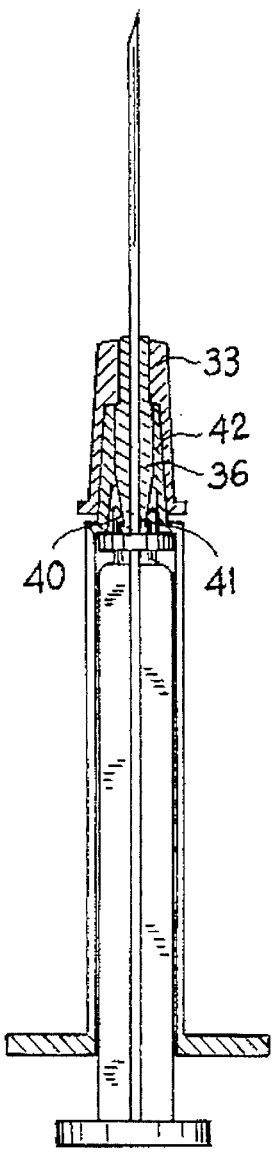
Figure 16:
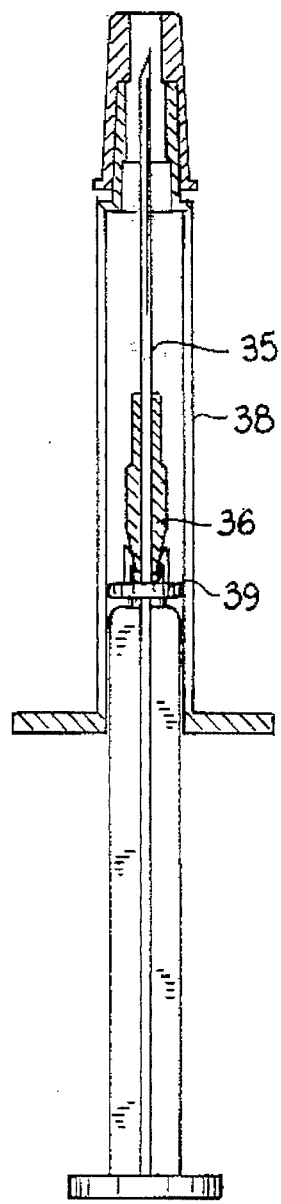

The suction needle of FIG. 10 and the hypodermic needle of FIG. 11 are used with a hypodermic syringe according to FIG. 9. As is typical, the hypodermic syringe of FIG. 9 comprises a cylindrical part 38 in which a movable piston 39 is received. The piston 39 comprises forward-oriented, hook-like flexible legs 40 and 41 with inward ridges 58, equivalent to the legs 11 and ridges 10 described above. In use, the suction needle of FIG. 10 is placed on the hypodermic syringe by sliding the hub 30 onto the distal portion 42 of the hypodermic syringe (see FIG. 12). After removing the protective cap 32, the suction needle 31 can be placed in a liquid and injection liquid 7 can be drawn into the syringe by retracting the piston 39 (FIG. 13). After removing the suction needle from the distal portion 42 of the syringe, the hypodermic needle of FIG. 11 is placed on the hypodermic syringe (FIG. 14). The protective cap 34 may then be removed, the needle placed in the patient, and the injection liquid introduced by displacing the piston forward (FIG. 15). As the piston is fully displaced to its distal end position, the flexible legs 40 and 41 expand over the peripheral ridge 44 in the connecting element 36 and then contract to cause the ridges 58 to engage the connecting element. In order to prevent the hypodermic needle from penetrating further into the body of the patient as a result of the distally oriented force exerted on the hypodermic needle during the forward movement of the piston, the friction between the hub 33 and the distal portion 42 of the hypodermic syringe is selected to ensure that the force required to cause the coupling between the connecting element 36 and the legs 40 and 41 is smaller than the friction force between the hub 33 and the distal portion 42. In addition, a collar 54, larger than the distal bore 56 in the hub 33, is provided on the connecting element 36 (FIG. 11) to block the forward movement of the connecting element in relation to the hub 33. When the piston 39 is retracted (FIG. 16), the piston carries the connecting element 36 and the needle 35 fixedly connected thereto inside the cylinder 38 of the hypodermic syringe, thus minimizing the danger of subsequent accidental pricking by a user.

While the embodiments shown in the figures feature the specific shapes therein described, the invention can obviously take other shapes with equivalent functionality and utility. In fact, any shape for any of the components that retains the functional characteristics described above provides an acceptable apparatus to practice the invention. The capacity of the syringe and the size of all other components can be varied in obvious ways to produce apparatus for different applications without affecting the scope of this disclosure. Similarly, a variety of other components could be used by one skilled in the art in conjunction with the syringe of the invention to fit the particular needs of specific applications.

Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What we claim as our invention is:

1. A hypodermic syringe apparatus comprising:

a cylinder having an integral distal portion for releasable connection with a hypodermic needle system;

a hypodermic-needle system consisting of a hypodermic-needle hub close-fittingly engaged in releasable connection with said distal portion of the cylinder; a connecting element releasably mounted in said hypodermic-needle hub; and a hypodermic needle threaded through and fixedly attached to said connecting element; and a piston displaceably mounted in said cylinder and comprising coupling means for connecting the piston and said connecting element in a distal position of the piston, said coupling means consisting of a plurality of flexible legs capable of gripping said connecting element.

2. The hypodermic syringe apparatus claimed in claim 1, wherein said flexible legs comprise inward ridges and said connecting element comprises a peripheral ridge for engagement with said inward ridges.

3. A hypodermic syringe apparatus comprising:

a cylinder having an integral distal portion for releasable connection with a hypodermic needle system;

a hypodermic-needle system consisting of a hypodermic-needle hub close-fittingly engaged in releasable connection with said distal portion of the cylinder; a connecting element releasably mounted in said hypodermic-needle hub; and a hypodermic needle threaded through and fixedly attached to said connecting element; and a piston displaceably mounted in said cylinder and comprising coupling means for connecting piston and said connecting element in a distal position of the piston, wherein said hypodermic-needle hub has a longitudinal distal bore; said connecting element has a distal portion releasably mounted in said longitudinal distal bore in the hypodermic-needle hub, has a proximal end, and has a longitudinal bore therethrough; and said hypodermic needle is threaded through and fixedly attached to said longitudinal bore in the connecting element; and wherein said coupling means consists of flexible legs capable of gripping the proximal end of said connecting element.

4. The hypodermic syringe apparatus claimed in claim 3, wherein said flexible legs comprise inward ridges and said proximal end of the connecting element comprises a peripheral ridge for engagement with said inward ridges in the flexible legs.

5. A hypodermic syringe apparatus comprising, in combination:

a cylinder having a distal portion for releasable connection with a hypodermic needle system;

a hypodermic-needle system consisting of a hub close-fittingly engaged in releasable connection with said distal portion of the cylinder; and a hypodermic needle slidably mounted in said hub and having a flattened proximal end with a plurality of notches, said proximal end projecting inside said distal portion of the cylinder; and a piston displaceably mounted in said cylinder and comprising coupling means for connecting the piston and said plurality of notches in the proximal end of the needle wherein said proximal end of the hypodermic needle is flattened to form two flat sides and contains a plurality of notches for engagement with said coupling means.

6. A hypodermic syringe apparatus comprising:

a cylinder having an integral distal portion releasably connected to a hypodermic needle system;

a hypodermic-needle system consisting of a hypodermic-needle hub close-fittingly engaged in releasable connection with an exterior surface of said distal portion of the cylinder; a connecting element releasably engaged by said hypodermic-needle hub; and a hypodermic needle threaded through and fixedly attached to said connecting element; and a piston displaceably mounted in said cylinder and comprising coupling means for connecting the piston and said connecting element in a distal position of the piston, said coupling means consisting of a single-piece member integral with said piston;

wherein said coupling means consists of a plurality of flexible legs capable of gripping said connecting element.

7. The hypodermic syringe apparatus claimed in claim 6, wherein said hypodermic-needle hub has a longitudinal distal bore; said connecting element has a distal portion releasably mounted in said longitudinal distal bore in the hypodermic-needle hub, has a proximal end, and has a longitudinal bore therethrough; and said hypodermic needle is threaded through and fixedly attached to said longitudinal bore in the connecting element.

8. The hypodermic syringe apparatus claimed in claim 7, wherein said flexible legs comprise inward ridges and said proximal end of the connecting element comprises a peripheral ridge for engagement with said inward ridges in the flexible legs.

9. The hypodermic syringe apparatus claimed in claim 6, wherein said flexible legs comprise inward ridges and said connecting element comprises a peripheral ridge for engagement with said inward ridges.

10. A hypodermic syringe apparatus comprising, in combination:

a cylinder having a distal portion for releasable connection with a hypodermic needle system;

a hypodermic-needle system consisting of a hub releasably connected to an exterior surface of said distal portion of the cylinder; and a hypodermic needle slidably mounted in said huh and having a proximal end with at least one notch, said proximal end projecting inside said distal portion of the cylinder; and a piston displaceably mounted in said cylinder and comprising coupling means for connecting the piston and said at least one notch in the proximal end of the needle;

wherein said proximal end of the hypodermic needle is flattened to form two flat sides and contains a plurality of notches for engagement with said coupling means.

* * * * *